United States Patent [19]

Alam et al.

[11] Patent Number: 5,036,060
[45] Date of Patent: Jul. 30, 1991

[54] CYCLOPHOSPHAMIDE

[75] Inventors: Abu S. Alam, Libertyville; Fakrul A. A. Sayeed, Mundelein; Kenneth J. Koziol, Bensenville; John N. Kapoor, Lake Forest, all of Ill.

[73] Assignee: Fujisawa USA, Inc., Deerfield, Ill.

[21] Appl. No.: 442,486

[22] Filed: Nov. 24, 1989

Related U.S. Application Data

[63] Continuation of Ser. No. 223,919, Jul. 25, 1988, abandoned.

[51] Int. Cl.$^5$ ............................................. A61K 31/66
[52] U.S. Cl. ................................................... 514/110
[58] Field of Search ......................................... 514/110

[56] References Cited

U.S. PATENT DOCUMENTS 4,537,883  8/1985  Alexander et al. ................. 514/110

FOREIGN PATENT DOCUMENTS 2084154  4/1982  United Kingdom ................ 514/110

OTHER PUBLICATIONS

PDR, 35th Ed, 1981, pp. 1131–1132.

Primary Examiner—Jerome D. Goldberg
Attorney, Agent, or Firm—W. Dennis Drehkoff

[57] ABSTRACT

A mannitol-free lyophilized formulation of cyclophosphamide is disclosed. Sodium chloride is present as an excipient.

5 Claims, No Drawings

CYCLOPHOSPHAMIDE

This application is a continuation of application Ser. No. 223,919, filed July 25, 1988 now abandoned.

BACKGROUND OF THE INVENTION

This invention relates generally to the field of antineoplastic agents and more specifically to cyclophosphamide and formulations thereof suitable for use in parenteral administration.

Cyclophosphamide is one of the most significant antineoplastic drugs of today. Cyclophosphamide is disclosed and claimed in U.S. Pat. No. 3,018,302 granted Jan. 23, 1962 to H. Arnold et al., and is denoted chemically as 2-[bis(2-chloroethyl)amino]tetrahydro-2H-1,3,2-oxazaphosphorine -2-oxide monohydrate.

Cyclophosphamide was initially commercially available as the monohydrate, in a parenteral dosage pre-mix consisting of a sterile, packaged, dry-powder admixture of the drug and sodium chloride. The premix was dissolved in water prior to administration which could be oral as well as parenteral.

The aqueous solution, however, necessitated prompt administration in that shelf-life was limited to several hours after preparation. Moreover, during processing and/or storage of the dry-powder pre-mix formulation, a glassiness and/or stickiness could be acquired by the pre-mix composition giving an unattractive material with inferior solubility characteristics and decreased potency. This deterioration was more pronounced as storage time was extended or if the upper limit of the storage temperature range was exceeded. This temperature sensitivity was problematic since common practice was to dissolve the solid cyclophosphamide pre-mix by heating the mixture, to expedite the dissolution process.

More recently, cyclophosphamide has become available as a lyophilizate. Although lyophilization is often employed for injectable pharmaceuticals which exhibit poor stability in aqueous solution, lyophilization was not applied to cyclophosphamide until around 1982.

As noted in Remington's "[t]he active constituent of many pharmaceutical preparations is present in such small quantities that if freeze-dried alone its presence would be hard to detect visually. Therefore, excipients are often added to increase the amount of solids present." Some such excipients which find common use are sodium or potassium phosphates, citric acid, tartaric acid, gelatin and carbohydrates such as dextrose, mannitol and dextran.

U.S. Pat. No. 4,537,883, issued to R. L. Alexander et al. pertains to a lyophilized cyclophosphamide. The '883 patent indicates that a storage-stable, lyophilized cyclophosphamide can be achieved provided that the lyophilizate retains some water of hydration and provided that mannitol is used as the sole excipient. More specifically, the lyophilized cyclophosphamide-mannitol solid composition of the '883 patent is alleged to have improved thermal stability when it contains an amount of water approximately equimolar to the cyclophosphamide content, taken as the anhydride. More importantly, the '883 patent states at column 3, lines 52-55, that the desirable, physical properties of the solid composition appear to be achieved only by using mannitol as the major excipient.

The '883 patent details an investigation of twelve different excipients, other than mannitol, which were used in attempts to produce a lyophilized cyclophosphamide, all unsuccessfully. Further, the '883 patent details the investigation of combinations of various excipients, none of which were useful in producing a usable lyophilized cyclophosphamide, except for certain combinations in which mannitol was the principal excipient.

Although the lyophilized formulations of cyclophosphamide, as shown in the '883 patent, have found commercial acceptance, a need continues to exist for alternate formulations of cyclophosphamide which do not require the presence of mannitol.

SUMMARY OF THE INVENTION

It has now been discovered that cyclophosphamide can be lyophilized without the use of mannitol, by using sodium chloride as the excipient.

It certainly is surprising that a stable lyophilizate of cyclophosphamide can be formed by use of sodium chloride as the excipient. These unexpected results are directly at odds with the '883 patent, which states that mannitol is the only excipient that is capable of imparting suitable stability and physical characteristics to a lyophilized cyclophosphamide formulation.

Further, as shown subsequently in Comparative Example A, when sodium chloride was substituted for a portion of mannitol, so that a combination of the two was employed as the excipient during lyophilization, the result was unsatisfactory. This makes the discovery that all of the mannitol can be replaced with sodium chloride, as the lyophilization excipient, even more surprising.

DETAILED DESCRIPTION OF THE INVENTION

In accordance with the present invention an aqueous, sterile, pre-lyophilization solution is first formed having a cyclophosphamide concentration from about 0.5 to about 3.5 percent. Using standard lyophilization techniques, well known in the art, the solution is lyophilized until a moisture content in the range of 3.0 to about 8.0 percent is achieved. This moisture content should equate to from about 0.5 to about 1.5 moles of water per mole of cyclophosphamide, preferably 1.0 mole. The resulting lyophilizate is storage-stable and can be readily reconstituted with water-for-injection, or other suitable carrier, to provide liquid formulations of cyclophosphamide, suitable for parenteral injection.

The pre-lyophilization solution is first formed by charging a suitable compounding vessel with water, preferably Water for Injection, USP, and the desired amount of cyclophosphamide, USP. The cyclophosphamide is allowed to dissolve, preferably with stirring, and if necessary additional Water for Injection, USP is added to effect a solution. The concentration of the cyclophosphamide in the pre-lyophilization solution is not critical, but usually is from about 0.5 to about 3.5 parts by weight, of cyclophosphamide, per 100 parts of water. Preferably the cyclophosphamide is present in an amount from about 0.5 to about 3.5 parts; most preferably the cyclophosphamide is present in an amount of about 3.33 parts, per 100 parts of water. All parts of cyclophosphamide, are on a weight basis, as the anhydride. Accordingly, in weighing the cyclophosphamide to be used in the pre-lyophilization solution, the amount of moisture in the product must first be calculated and the weight of cyclophosphamide adjusted accordingly, to take into account the presence of moisture in the product.

A suitable amount of sodium chloride should then be added to the cyclophosphamide solution and preferably mixed until a solution is effected. The vessel may then be filled to the desired final volume with water, preferably with Water for Injection, USP, that is at or about room temperature. The solution may then be mixed. Mixing should be sufficient to dissolve the cyclophosphamide, which usually takes about 10 minutes or more. The amount of sodium chloride employed is usually from about 0.1 to about 3 parts, by weight, per 100 parts of water, in the pre-lyophilization solution. The relative weight ratio of cyclophosphamide to sodium chloride is from about 50–75 parts of cyclophosphamide: 20–40 parts of sodium chloride. Most typically, the amount of cyclophosphamide employed is about 3.3 parts per hundred parts of water and the amount of sodium chloride employed is about 1.5 parts, per 100 parts of water, in the pre-lyophilization formulation.

Following the combination of the water, the cyclophosphamide, and the sodium chloride, the solution should have a pH in the range of 2.0 to 7.0. More specifically, the pH should be at or about 4.5.

The pre-lyophilization solution should be sterilized prior to lyophilization, sterilization is generally performed by filtration, through a 0.22 micron filter.

After sterilization, the solution is ready for lyophilization. Generally, the purified solution will be introduced into a sterile receiving vessel, and then transferred to any suitable container or containers in which the formulation may be effectively lyophilized. Usually the formulation is effectively and efficiently lyophilized in the containers in which the product is to be marketed.

The lyophilization process is well known to those skilled in the art and should be readily adaptable for use with respect to the present invention. A typical procedure for use in lyophilizing the pre-lyophilization solutions is set forth below. However, no criticality is attached to the exact procedure and it would be obvious to one skilled in the art that modifications thereto may be made.

Initially, the product is placed in a lyophilization chamber and subjected to temperatures well below the product's freezing point, generally for several hours. Preferably, the temperature will be at or below −40° C. for at least 2 hours. After freezing is complete, the chamber and the condenser are evacuated, the condenser surface having been previously chilled by circulating refrigerant. Preferably, the condenser will have been chilled to about −60° C. or below. Additionally, evacuation of the chamber should continue until a pressure of 75–150 microns is obtained.

The product composition is then warmed. This usually will be carried out by warming the shelves within the lyophilizer on which the product rests during the lyophilization process. The warming process will optimally take place very gradually, over the course of several hours. For example, the shelf temperature should initially be increased to about −30° C. and maintained for 12–18 hours. Then the shelf temperature should be increased to 25° C. and maintained for 8–16 hours.

The drying cycle having been completed, it is then advisable to bleed the chamber slowly to atmospheric pressure with sterile, dry nitrogen gas. If the product composition has been lyophilized in containers such as vials, the vials are removed and immediately sealed. Several representative samples should be removed for purposes of performing moisture analysis. During the course of the moisture analysis the remaining product should be maintained in the chamber under a dry, sterile atmosphere, preferably nitrogen gas, and chilled, preferably at a shelf temperature of about −27° C.

It is important for purposes of stability that the product composition not be overly dried. The average percent moisture should be in the rang of about 3.0 to about 8.0 percent water, preferably in the range of about 4.5 to about 5.9 percent water. If the average percent water exceeds these limits, the drying cycle should be continued for an additional period of time. If, however, the composition is overly dried, then the product is rejected.

It is desired that the cyclophosphamide in the lyophilized product be approximately in the form of its monohydrate. Thus, it is desirable that the amount of water be approximately equimolar to the cyclophosphamide. Some deviation from that goal may be tolerated, so that the amount of water may range from about 0.5 to about 1.5 moles, per mole of cyclophosphamide. However, as indicated, it is desirable that the amount of water be approximately equimolar to the cyclophosphamide.

The cyclophosphamide formulation is typically marketed in unit dosage forms. The unit dosage forms of the present invention, although typically in the form of a vial, may be any suitable container, such as ampoules, syringes, covials, which is capable of maintaining a sterile environment and being capable of being hermetically sealed, as by a stopper. Such containers are usually glass, although they may also be of plastic, provided that the plastic does not interact with the cyclophosphamide formulation. The closure is typically a stopper, most typically a sterile rubber stopper which affords a hermetic seal. Most typically, the unit dosage form is a vial having a size from about 5 ml to about 250 ml.

The cyclophosphamide, after lyophilization, may be filled into containers, such as vials, or, more preferably, the prelyophilization solution is filled into such vials and is lyophilized therein, resulting in vials which directly contain the lyophilized cyclophosphamide formulation. Such vials are, after filling or lyophilization of the solution therein, sealed, as with a stopper, to provide a sealed, sterile, unit dosage form.

The lyophilized cyclophosphamide formulations of the present invention may be reconstituted with water, preferably Water for Injection, USP, or other sterile fluid, to provide an appropriate solution of cyclophosphamide for administration, as through parenteral injection.

The present invention will be further understood by reference to the following nonlimiting examples. It will be apparent to those skilled in the art that modifications of both methods and material may be employed, without departing from the scope of the present invention.

COMPARATIVE EXAMPLE A

This example demonstrates an attempt to prepare a lyophilized cyclophosphamide formulation using a combination of sodium chloride and mannitol as excipients.

A suitable compounding vessel was charged with 8 liters of room temperature water for injection, USP. To the water was added 333.3 grams of cyclophosphamide, USP, based on the anhydride content, and the mixture was stirred for approximately 10 minutes. The vessel was filled to a level of 9.5 liters with room temperature Water for Injection, USP, and mixed until the cyclophosphamide was completely dissolved, over a period of approximately 30 minutes. One hundred fifty grams of sodium chloride was added to the solution and mixed until completely dissolved, over a period of approximately 15 minutes. Then, 120 grams of mannitol, USP, was added to the solution and mixed, again until dissolved, taking approximately an additional 15 minutes. Water for Injection was then added to the solution to achieve a final volume of 10 liters, and the entire solution mixed for approximately 10 minutes. The resultant solution was then filtered through a sterile 0.22 micron filter into a clean, sterile, receiving vessel, and filled into 20 milliliter vials to a fill volume of 6.4±0.1 ml.

The vials were then loaded into a lyophilizer chamber using bottomless trays. Thermocouples were placed in representative vials on different shelves and the chamber door closed. The freezing process was then begun and a temperature of below −40° C. was maintained for approximately 2 hours. The shelf temperature was then set to −20° C. and when the product attained the temperature of −20° C.±2° C., the cycle was continued for between two and four hours. Then, the product was refrozen such that the thermocouples registered a temperature below −40° C. for between one and four hours. The condenser was then activated and allowed to reach a temperature of −60° C. or below at which time a vacuum was pulled until the chamber achieved a level of 75-150 microns. The shelf temperature was adjusted to −30° C. and when the thermocouples attained a temperature of −32° C.±2° C., the cycle was continued for between 22 and 26 hours. The shelf temperature was set to −25° C. and when the thermocouples were at a temperature of −27° C.±2° C., the cycle was continued for between 14 and 24 hours. After completion of the drying cycle the lyophilization chamber was isolated and bled solely with sterile dry nitrogen gas until atmospheric temperature was reached.

Three representative vials were removed from each shelf, immediately sealed, and analyzed for the moisture content which was found to be between 4.5 and 5.9 percent. At that time the lyophilization chamber was opened to the condenser, which was set at a temperature of −60° C. or below, and a vacuum of 125±25 microns was pulled, maintaining the shelf temperature setting of −20° C. These parameters were maintained for 30±10 minutes after which the lyophilization chamber was isolated and the chamber bled slowly with sterile nitrogen gas until atmospheric pressure was achieved. At that time all vials were stoppered, removed from the lyophilizer and appropriately capped.

Representative vials were then used in long term storage tests at temperatures of approximately 4° C., room temperature, 30° C. and 40° C. The results of those storage tests are shown in Tables 1 through 4, respectively. From an analysis of the long term storage results, it is clear that the cyclophosphamide lyophilizate made using a combination of sodium chloride and mannitol as excipients was not sufficiently storage-stable to be commercially acceptable.

EXAMPLE I

This example demonstrates the production of a cyclophosphamide lyophilizate within the scope of the present invention, placed into unit dosage forms which were 20 milliliter vials, filled to a level of 6.4±0.1 ml, to yield 200 mg cyclophosphamide per vial.

A suitable compounding vessel was charged with 8 liters of room temperature Water for Injection, USP. To the Water was added 333.3 grams of cyclophosphamide, USP and the mixture was stirred for 10 minutes. The vessel was filled to a volume of 9.5 liters with room temperature Water for Injection USP, and the solution was mixed until the cyclophosphamide, USP was completely dissolved to solution. 150.0 grams of sodium chloride, USP was added to the solution and mixed until completely dissolved. The vessel was filled to a final volume of 10 liters with room temperature Water for Injection, USP, and mixed for approximately 10 minutes. The pH was then checked and found to be within the limits of 3.3 to 5.8. Similarly, the temperature was checked and was found to be within the limits of 15°-25° C. The solution was filtered through a sterile 0.22 micron filter into a clean, sterile receiving vessel and the used to fill 20 ml vials to a level of 6.4±0.1 ml. vials. Once filling was completed, the product, in vials was lyophilized.

The product was frozen at or below −40° C. for approximately 2 hours. The shelf temperature was set to −20° C. and maintained for 1 to 3 hours. The product was frozen again at −40° C. or below for between 1 and 4 hours. The condenser was then cooled to −60° C. or below. Vacuum was established, and the chamber achieved the pressure of 75-150 microns. The shelf temperature was set at −30° C. When the product thermocouples had attained −32°±2° C. the cycle was continued for between 12 and 18 hours. The shelf temperature was then set at −25° C. When the product thermocouples attained −27° C.±2° C. the cycle was continued for between 8 and 16 hours. After completion of the drying cycle, the lyophilization chamber was isolated and bled slowly with sterile, dry nitrogen gas to atmospheric pressure. The sample vials were removed and immediately sealed. Moisture analyses were then performed. While moisture analyses were in process, the lyophilization chamber was closed, while maintaining a shelf temperature of −27° C.

The drying cycle was continued until the product moisture was 4.5-5.9 percent. The lyophilization chamber was then opened to the condenser, and vacuum was pulled (125±25 microns), while maintaining a shelf temperature of −20° C. Those parameters were maintained for 30±10 minutes. The lyophilization chamber then was isolated and bled slowly with sterile, dry nitrogen gas until atmospheric pressure was achieved.

All vials were stoppered in the lyophilizer chamber, and then removed from the lyophilizer and capped.

Vials were then selected and placed into long-term storage stability tests at approximately 4° C., room temperature, 30° C., and 40° C. The results of that long term storage stability testing are shown in Tables V-VIII.

From analyzing the data contained in the aforementioned tables, it is clear that the cyclophosphamide lyophilizate obtained through the use of sodium chloride meets the requisite standards for being a commercial product. The results are certainly dramatic and surprising, especially when they are compared to the results shown with respect to the long term storage stability testing from Example A, for the product wherein a combination of sodium chloride and mannitol was used as excipients during the lyophilization process.

EXAMPLE II

In accordance with the procedure set forth in Example I, a cyclophosphamide lyophilizate was produced, using the identical quantities of cyclophosphamide, sodium chloride, and water, as set forth with respect to Example I and an identical manufacturing procedure was employed. Again, representative samples were placed in long term storage tests at temperatures of approximately 4° C., room temperature, 30° C., and 40° C. The results of that long term storage stability testing is set forth in Tables I through XII.

As can be seen by reference to the aforementioned tables, the present example produced a lyophilized cyclophosphamide formulation having suitable storage stability for use as a commercial product.

EXAMPLE III

In accordance with the procedure set forth for Example I, a lyophilized cyclophosphamide formulation was prepared, using quantities of cyclosphophamide, sodium chloride, and water, identical to that set forth in Example I. However, the resulting pre-lyophilization solution was filled into 10 milliliter vials, rather than 20 ml vials, to a fill volume of 3.2±0.1 ml, resulting in a dosage of 100 mg/vial.

After lyophilization, selected vials were placed into long term storage testing at temperatures of approximately 4° C., room temperature, 30° C. and 40° C. The results of that testing are set forth in Tables XIII through XVI.

As may be seen, our reference to the data obtained in the aforementioned tables, the lyophilized cyclophosphamide was sufficiently stable upon long term storage to be useful as a commercial product.

EXAMPLE IV

In accordance with the procedure set forth for Example I, a lyophilized cyclophosphamide formulation was prepared, using cyclophosphamide, sodium chloride, and water, in the same quantities as set forth with respect to Example I. However, the pre-lyophilization solution was filled into 30 milliliter vials to a level of 16.0±0.1 ml, resulting in a dosage of 500 mg/vial.

Vials were selected for long term storage testing at temperatures of approximately 4° C., room temperature, 30° C. and 40° C. The results of that storage testing is set forth in Tables XVII through XX. As can be ascertained by reviewing the results set forth in the aforementioned tables, the lyophilized cyclophosphamide formulation of the present invention was sufficiently stable for use as a commercial product.

EXAMPLE V

In accordance with the procedure discussed with respect to Example V, lyophilized cyclophosphamide was prepared in 30 ml vials, with each vial containing 500 mg/vial of cyclophosphamide. Vials were selected for long term storage stability testing at temperatures of approximately 4° C., room temperature, 30° C. and 40° C. The results of that storage testing is set forth in Tables XX through XXIV.

As may be ascertained from reviewing the data set forth in the aforementioned tables, the lyophilized cyclophosphamide of the present invention was found to be sufficiently storage stable for use as a commercial product.

TABLE I

STABILITY TESTING SUMMARY
Cyclophosphamide/NaCl/Mannitol - Example A
Storage Temperature: 4° C.

| Tested/Analyzed for | 0 Month | 1 Month | 2 Months | 3 Months |
|---|---|---|---|---|
| Color/Clarity | Colorless/ | — | — | Colorless/ |
| (Reconstituted) | Clear | | | Clear |
| pH (Reconstituted) | 3.6 | — | — | 3.7 |
| Assay Cyclophosphamide (Reconstituted) | 100.6 | — | — | 104.6 |

TABLE II

STABILITY TESTING SUMMARY
Cyclophosphamide/NaCl/Mannitol - Example A
Storage Temperature: Room Temperature

| Tested/Analyzed for | 0 Month | 1 Month | 2 Months | 3 Months |
|---|---|---|---|---|
| Color/Clarity (Reconstituted) | Colorless/Clear | — | Colorless/Clear | Colorless/Clear |
| pH (Reconstituted) | 3.6 | — | 3.6 | 3.4 |
| Assay Cyclophosphamide (Reconstituted) | 100.6 | — | 89.8 | 86.6 |

TABLE III

STABILITY TESTING SUMMARY
Cyclophosphamide/NaCl/Mannitol - Example A
Storage Temperature: 30° C.

| Tested/Analyzed for | 0 Month | 1 Month | 2 Months | 3 Months |
|---|---|---|---|---|
| Color/Clarity (Reconstituted) | Colorless/Clear | — | Colorless/Clear | Colorless/Clear |
| pH (Reconstituted) | 3.6 | — | 3.4 | 3.0 |
| Assay Cyclophosphamide (Reconstituted) | 100.6 | — | 89.0 | 56.5 |

TABLE IV

STABILITY TESTING SUMMARY
Cyclophosphamide/NaCl/Mannitol - Example A
Storage Temperature: 40° C.

| Tested/Analyzed for | 0 Month | 1 Month | 2 Months | 3 Months |
|---|---|---|---|---|
| Color/Clarity (Reconstituted) | Colorless/Clear | — | Colorless/Clear | Colorless/Clear |
| pH (Reconstituted) | 3.6 | — | 2.5 | 2.3 |
| Assay Cyclophosphamide (Reconstituted) | 100.6 | — | 10.7 | 2.6 |

TABLE V

STABILITY TESTING SUMMARY
Cyclophosphamide/NaCl - Example I
Storage Temperature: 4° C.

| Tested/Analyzed for | 0 Month | 1 Month | 2 Months | 3 Months |
|---|---|---|---|---|
| Color/Clarity (Reconstituted) | Colorless/Clear | Colorless/Clear | — | Colorless/Clear |
| pH (Reconstituted) | 4.2 | 4.1 | — | 4.2 |
| Assay Cyclophosphamide | 102.9 | 101.5 | — | 103.2 |

TABLE V-continued

STABILITY TESTING SUMMARY
Cyclophosphamide/NaCl - Example I
Storage Temperature: 4° C.

| Tested/<br>Analyzed for | 0 Month | 1 Month | 2 Months | 3 Months |
|---|---|---|---|---|
| (Reconstituted) | | | | |

TABLE VI

STABILITY TESTING SUMMARY
Cyclophosphamide/NaCl - Example I
Storage Temperature: Room Temperature

| Tested/<br>Analyzed for | 0 Month | 1 Month | 2 Months | 3 Months |
|---|---|---|---|---|
| Color/Clarity<br>(Reconstituted) | Colorless/<br>Clear | Colorless/<br>Clear | Colorless/<br>Clear | Colorless/<br>Clear |
| pH (Reconstituted) | 4.2 | 4.1 | 4.1 | 4.1 |
| Assay<br>Cyclophosphamide<br>(Reconstituted) | 102.9 | 101.9 | 102.4 | 103.1 |

TABLE VII

STABILITY TESTING SUMMARY
Cyclophosphamide/NaCl - Example I
Storage Temperature: 30° C.

| Tested/<br>Analyzed for | 0 Month | 1 Month | 2 Months | 3 Months |
|---|---|---|---|---|
| Color/Clarity<br>(Reconstituted) | Colorless/<br>Clear | Colorless/<br>Clear | Colorless/<br>Clear | Colorless/<br>Clear |
| pH (Reconstituted) | 4.2 | 4.1 | 4.1 | 4.0 |
| Assay<br>Cyclophosphamide<br>(Reconstituted) | 102.9 | 101.7 | 101.5 | 99.7 |

TABLE VIII

STABILITY TESTING SUMMARY
Cyclophosphamide/NaCl - Example I
Storage Temperature: 40° C.

| Tested/<br>Analyzed for | 0 Month | 1 Month | 2 Months | 3 Months |
|---|---|---|---|---|
| Color/Clarity<br>(Reconstituted) | Colorless/<br>Clear | Colorless/<br>Clear | Colorless/<br>Clear | Colorless/<br>Clear |
| pH (Reconstituted) | 4.2 | 4.0 | 3.9 | 3.5 |
| Assay<br>Cyclophosphamide<br>(Reconstituted) | 102.9 | 101.3 | 101.1 | 101.3 |

TABLE IX

STABILITY TESTING SUMMARY
Cyclophosphamide/NaCl - Example II
Storage Temperature: 4° C.

| Tested/<br>Analyzed for | 0 Month | 1 Month | 2 Months | 3 Months |
|---|---|---|---|---|
| Color/Clarity<br>(Reconstituted) | Colorless/<br>Clear | Colorless/<br>Clear | Colorless/<br>Clear | Colorless/<br>Clear |
| pH (Reconstituted) | 4.4 | 4.4 | 4.5 | 4.3 |
| Assay | 99.4 | 98.8 | 100.5 | 101.9 |

TABLE IX-continued

STABILITY TESTING SUMMARY
Cyclophosphamide/NaCl - Example II
Storage Temperature: 4° C.

| Tested/<br>Analyzed for | 0 Month | 1 Month | 2 Months | 3 Months |
|---|---|---|---|---|
| Cyclophosphamide<br>(Reconstituted) | | | | |

TABLE X

STABILITY TESTING SUMMARY
Cyclophosphamide/NaCl - Example II
Storage Temperature: Room Temperature

| Tested/<br>Analyzed for | 0 Month | 1 Month | 2 Months | 3 Months |
|---|---|---|---|---|
| Color/Clarity<br>(Reconstituted) | Colorless/<br>Clear | Colorless/<br>Clear | Colorless/<br>Clear | Colorless/<br>Clear |
| pH (Reconstituted) | 4.4 | 4.3 | 4.4 | 4.2 |
| Assay<br>Cyclophosphamide<br>(Reconstituted) | 99.4 | 100.2 | 101.6 | 103.6 |

TABLE XI

STABILITY TESTING SUMMARY
Cyclophosphamide/NaCl - Example II
Storage Temperature: 30° C.

| Tested/<br>Analyzed for | 0 Month | 1 Month | 2 Months | 3 Months |
|---|---|---|---|---|
| Color/Clarity<br>(Reconstituted) | Colorless/<br>Clear | Colorless/<br>Clear | Colorless/<br>Clear | Colorless/<br>Clear |
| pH (Reconstituted) | 4.4 | 4.3 | 4.3 | 4.1 |
| Assay<br>Cyclophosphamide<br>(Reconstituted) | 99.4 | 99.9 | 100.0 | 101.4 |

TABLE XII

STABILITY TESTING SUMMARY
Cyclophosphamide/NaCl - Example II
Storage Temperature: 40° C.

| Tested/<br>Analyzed for | 0 Month | 1 Month | 2 Months | 3 Months |
|---|---|---|---|---|
| Color/Clarity<br>(Reconstituted) | Colorless/<br>Clear | Colorless/<br>Clear | Colorless/<br>Clear | Colorless/<br>Clear |
| pH (Reconstituted) | 4.4 | 4.3 | 4.0 | 3.7 |
| Assay<br>Cyclophosphamide<br>(Reconstituted) | 99.4 | 99.4 | 97.9 | 100.9 |

TABLE XIII

STABILITY TESTING SUMMARY
Cyclophosphamide/NaCl - Example III
Storage Temperature: 4° C.

| Tested/<br>Analyzed for | 0 Month | 1 Month | 2 Months | 3 Months |
|---|---|---|---|---|
| Color/Clarity<br>(Reconstituted) | Colorless/<br>Clear | Colorless/<br>Clear | Colorless/<br>Clear | Colorless/<br>Clear |

TABLE XIII-continued
STABILITY TESTING SUMMARY
Cyclophosphamide/NaCl - Example III
Storage Temperature: 4° C.

| Tested/Analyzed for | 0 Month | 1 Month | 2 Months | 3 Months |
|---|---|---|---|---|
| pH (Reconstituted) | 4.4 | 4.3 | 4.4 | 4.4 |
| Assay Cyclophosphamide (Reconstituted) | 98.7 | 98.2 | 99.2 | 99.5 |

TABLE XIV
STABILITY TESTING SUMMARY
Cyclophosphamide/NaCl - Example III
Storage Temperature: Room Temperature

| Tested/Analyzed for | 0 Month | 1 Month | 2 Months | 3 Months |
|---|---|---|---|---|
| Color/Clarity (Reconstituted) | Colorless/Clear | Colorless/Clear | Colorless/Clear | Colorless/Clear |
| pH (Reconstituted) | 4.4 | 4.3 | 4.5 | 4.2 |
| Assay Cyclophosphamide (Reconstituted) | 98.7 | 97.9 | 102.9 | 99.4 |

TABLE XV
STABILITY TESTING SUMMARY
Cyclophosphamide/NaCl - Example III
Storage Temperature: 30° C.

| Tested/Analyzed for | 0 Month | 1 Month | 2 Months | 3 Months |
|---|---|---|---|---|
| Color/Clarity (Reconstituted) | Colorless/Clear | Colorless/Clear | Colorless/Clear | Colorless/Clear |
| pH (Reconstituted) | 4.4 | 4.3 | 4.2 | 4.0 |
| Assay Cyclophosphamide (Reconstituted) | 98.7 | 98.0 | 102.4 | 97.6 |

TABLE XVI
STABILITY TESTING SUMMARY
Cyclophosphamide/NaCl - Example III
Storage Temperature: 40° C.

| Tested/Analyzed for | 0 Month | 1 Month | 2 Months | 3 Months |
|---|---|---|---|---|
| Color/Clarity (Reconstituted) | Colorless/Clear | Colorless/Clear | Colorless/Clear | Colorless/Clear |
| pH (Reconstituted) | 4.4 | 4.3 | 4.1 | 3.9 |
| Assay Cyclophosphamide (Reconstituted) | 98.7 | 101.2 | 97.2 | 99.1 |

TABLE XVII
STABILITY TESTING SUMMARY
Cyclophosphamide/NaCl - Example IV
Storage Temperature: 4° C.

| Tested/Analyzed for | 0 Month | 1 Month | 2 Months | 3 Months |
|---|---|---|---|---|
| Color/Clarity (Reconstituted) | Colorless/Clear | Colorless/Clear | — | — |
| pH (Reconstituted) | 4.1 | 4.0 | — | — |
| Assay Cyclophosphamide (Reconstituted) | 105.7 | 104.3 | — | — |

TABLE XVIII
STABILITY TESTING SUMMARY
Cyclophosphamide/NaCl - Example IV
Storage Temperature: Room Temperature

| Tested/Analyzed for | 0 Month | 1 Month | 2 Months | 3 Months |
|---|---|---|---|---|
| Color/Clarity (Reconstituted) | Colorless/Clear | Colorless/Clear | Colorless/Clear | Colorless/Clear |
| pH (Reconstituted) | 4.1 | 4.0 | 4.0 | 3.9 |
| Assay Cyclophosphamide (Reconstituted) | 105.7 | 100.6 | 102.4 | 101.7 |

TABLE XIX
STABILITY TESTING SUMMARY
Cyclophosphamide/NaCl - Example IV
Storage Temperature: 30° C.

| Tested/Analyzed for | 0 Month | 1 Month | 2 Months | 3 Months |
|---|---|---|---|---|
| Color/Clarity (Reconstituted) | Colorless/Clear | Colorless/Clear | Colorless/Clear | Colorless/Clear |
| pH (Reconstituted) | 4.1 | 4.0 | 4.0 | 3.8 |
| Assay Cyclophosphamide (Reconstituted) | 105.7 | 101.7 | 100.8 | 99.2 |

TABLE XX
STABILITY TESTING SUMMARY
Cyclophosphamide/NaCl - Example IV
Storage Temperature: 40° C.

| Tested/Analyzed for | 0 Month | 1 Month | 2 Months | 3 Months |
|---|---|---|---|---|
| Color/Clarity (Reconstituted) | Colorless/Clear | Colorless/Clear | Colorless/Clear | Colorless/Clear |
| pH (Reconstituted) | 4.1 | 3.9 | 3.9 | 3.7 |
| Assay Cyclophosphamide (Reconstituted) | 105.7 | 103.6 | 99.6 | 97.0 |

TABLE XXI
STABILITY TESTING SUMMARY
Cyclophosphamide/NaCl - Example V
Storage Temperature: 4° C.

| Tested/Analyzed for | 0 Month | 1 Month | 2 Months | 3 Months |
|---|---|---|---|---|
| Color Clarity | Colorless/ | — | — | — |

TABLE XXI-continued

STABILITY TESTING SUMMARY
Cyclophosphamide/NaCl - Example V
Storage Temperature: 4° C.

| Tested/Analyzed for | 0 Month | 1 Month | 2 Months | 3 Months |
|---|---|---|---|---|
| (Reconstituted) | Clear | | | |
| pH (Reconstituted) | 4.0 | 4.1 | — | — |
| Assay Cyclophosphamide (Reconstituted) | 106.0 | 106.3 | — | — |

TABLE XXII

STABILITY TESTING SUMMARY
Cyclophosphamide/NaCl - Example V
Storage Temperature: Room Temperature

| Tested/Analyzed for | 0 Month | 1 Month | 2 Months | 3 Months |
|---|---|---|---|---|
| Color/Clarity (Reconstituted) | Colorless/Clear | Colorless/Clear | Colorless/Clear | Colorless/Clear |
| pH (Reconstituted) | 4.0 | 4.0 | 3.9 | 3.9 |
| Assay Cyclophosphamide (Reconstituted) | 106.0 | 105.4 | 105.6 | 105.8 |

TABLE XXIII

STABILITY TESTING SUMMARY
Cyclophosphamide/NaCl - Example V
Storage Temperature: 30° C.

| Tested/Analyzed for | 0 Month | 1 Month | 2 Months | 3 Months |
|---|---|---|---|---|
| Color/Clarity (Reconstituted) | Colorless/Clear | Colorless/Clear | Colorless/Clear | Colorless/Clear |
| pH (Reconstituted) | 4.0 | 4.1 | 4.0 | 3.8 |
| Assay Cyclophosphamide (Reconstituted) | 106.0 | 105.7 | 105.4 | 106.3 |

TABLE XXIV

STABILITY TESTING SUMMARY
Cyclophosphamide/NaCl - Example V
Storage Temperature: 40° C.

| Tested/Analyzed for | 0 Month | 1 Month | 2 Months | 3 Months |
|---|---|---|---|---|
| Color/Clarity (Reconstituted) | Colorless/Clear | Colorless/Clear | Colorless/Clear | Colorless/Clear |
| pH (Reconstituted) | 4.0 | 3.9 | 3.7 | 3.4 |
| Assay Cyclophosphamide (Reconstituted) | 106.0 | 101.7 | 105.1 | 104.8 |

TABLE XXV

| Time (wks) | A | B | C | D |
|---|---|---|---|---|
| 3 | 104 | 96 | 93 | 95 |
| 6 | 102 | 57 | 39 | 37 |
| 12 | 101 | 42 | 4 | — |

Comparative Stabilities at 40° C. for:
A. Cyclophosphamide/Mannitol Lyophilizate
B. Cyclophosphamide/Mannitol Blend
C. Cyclophosphamide/Sodium Chloride Blend
D. Cyclophosphamide

What is claimed is:

1. A pharmaceutical composition comprising cyclosphosphamide and sodium chloride as a sterile, lyophilized product wherein (1) the composition is free of mannitol, (2) the relative weight ratio of cyclophosphamide to sodium chloride is about 50–75 parts cyclophosphamide: 20–40 parts sodium chloride, and (3) from about 0.5 to about 1.5 moles of water are present per mole of cyclophosphamide.

2. A pharmaceutical composition consisting essentially of cyclophosphamide and sodium chloride, as a lyophilizate stabilized by an antioxidant selected from the group consisting of sodium metabisulfite and ascorbic acid, in a pharmaceutically acceptable amount from about 0.1 to about 2 percent wherein (1) the composition is free of mannitol, (2) the relative weight ratio of cyclophosphamide to sodium chloride is about 50–75 parts cyclophosphamide: 20–40 parts sodium chloride, and (3) from about 0.5 to about 1.5 moles of water are present per mole of cyclophosphamide.

3. A pharmaceutical composition consisting essentially of cyclophosphamide and sodium chloride, as a lyophilizate, stabilized by a chelating agent selected from the group consisting of ethylenediaminetetraacetate and citric acid, in a pharmaceutically acceptable amount from about 0.1 to about 5 percent wherein (1) the composition is free of mannitol, (2) the relative weight ratio of cyclophosphamide to sodium chloride is about 50–75 parts cyclophosphamide: 20–40 parts sodium chloride, and (3) from about 0.5 to about 1.5 moles of water are present per mole of cyclophosphamide.

4. A pharmaceutical composition consisting essentially of cyclophosphamide and sodium chloride as a sterile, lyophilized product, wherein (1) the composition is free of mannitol, (2) the relative weight ratio of cyclophosphamide to sodium chloride is about 50–75 parts of cyclophosphamide; 20–40 parts of sodium chloride, and (3) from about 0.5 to about 1.5 moles of water are present per mole of cyclosphosphamide, the composition being preserved by a microbial agent selected from the group consisting of methylparaben, propylparaben, benzyl alcohol and chlorobutanol.

5. The composition of claim 4 wherein methyl paraben and propyl paraben are used in combination, methyl paraben being present in an amount from about 1 to about 3 percent and propyl paraben being present in an amount from about 0.05 to about 0.5 percent.

* * * * *